United States Patent [19]
Lacefield et al.

[11] 3,939,278
[45] Feb. 17, 1976

[54] PHENOXYPHENYL-ACETYLENES AND THIO ANALOGUES THEREOF AS ANTITHROMBOTIC AGENTS

[75] Inventors: William B. Lacefield; Winston S. Marshall, both of Indianapolis, Ind.

[73] Assignee: Eli Lilly and Company, Indianapolis, Ind.

[22] Filed: July 5, 1974

[21] Appl. No.: 485,878

[52] U.S. Cl. ................ 424/340; 424/341; 424/337
[51] Int. Cl.$^2$ ................ A61K 31/085; A61K 31/09; A61K 31/10
[58] Field of Search ............................ 424/340, 341

[56] References Cited
UNITED STATES PATENTS

| | | | |
|---|---|---|---|
| 3,764,702 | 10/1973 | Malen et al. | 424/317 |
| 3,840,604 | 10/1974 | Chodnekar et al. | 424/340 |

*Primary Examiner*—Donald B. Moyer
*Attorney, Agent, or Firm*—William E. Maycock; Everet F. Smith

[57] ABSTRACT

A method of treating vascular thrombosis in warm-blooded animals, employing a phenoxyphenylacetylene or thio analogue thereof as the active antithrombotic agent.

4 Claims, No Drawings

PHENOXYPHENYL-ACETYLENES AND THIO ANALOGUES THEREOF AS ANTITHROMBOTIC AGENTS

BACKGROUND OF THE INVENTION

This invention relates to a method of treating vascular thrombosis in warm-blooded animals, employing a phenoxyphenylacetylene or thio analogue thereof as the active antithrombotic agent.

A thrombus generally is defined as an obstruction, formed from components of blood, within the vascular system. When a thrombus is either free-floating in the blood stream or has been removed by the blood stream to a new location, it is referred to as an embolus. Thrombosis, which refers to the formation, development, or presence of a thrombus, is responsible for a variety of disorders which generally are termed thromboembolic diseases. Such diseases include phlebothrombosis, thrombophlebitis, pulmonary embolism, retinal thrombosis, myocardial infarction, and cerebral infarction, among others. More generally, such diseases can be considered to result from a vascular thrombosis, i.e., a thrombus within the vascular system of the body.

The chemoprophylactic or chemotherapeutic management of thromboembolic diseases generally involves compounds which fall into one of three categories: (1) platelet aggregation inhibitors, (2) anticoagulants, and (3) fibrinolytic agents. The chemotherapeutic use of fibrinolytic agents is based upon the fact that fibrin frequently forms the primary structural support of a thrombus. Dissolution of the fibrin should result in lysis of the thrombus, with restoration of blood flow. Anticoagulants and platelet aggregation inhibitors, on the other hand, generally are employed prophylactically. Anticoagulants are more effective in the treatment of venous thrombosis than arterial thrombosis. The successful prophylaxis of arterial thrombosis must deal with the etiologic role of the platelet. The value of platelet function inhibitors in venous thrombosis, on the other hand, will be reflected by the extent to which platelets are involved in the formation of those thrombi. In any event, there are within the circulatory system regions of stasis in which fibrin formation would be virtually the sole factor in thrombosis, and other regions of high hemodynamic activity where the platelet nidus alone could block the vessel.

Consequently, the search for effective new platelet aggregation inhibitors continues to be an important research activity.

SUMMARY OF THE INVENTION

In accordance with the present invention, a method of treating vascular thrombosis in warm-blooded animals is provided which comprises administering to a warm-blooded animal in need of such treatment an effective amount of a phenoxyphenylacetylene or thio analogue thereof having the following general formula:

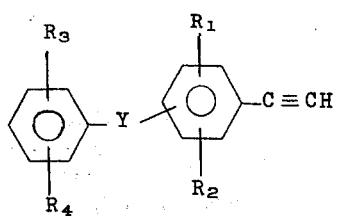

wherein $R_1$, $R_2$, $R_3$, and $R_4$ are monovalent groups independently selected from the group consisting of hydrogen, halo, $C_1$–$C_3$ alkyl, and $C_1$–$C_3$ alkoxy; and Y is oxygen or sulfur.

DETAILED DESCRIPTION OF THE INVENTION

As used herein, the term "treatment" is meant to include both active treatment and preventive or prophylactic treatment. Additionally, the term "halo" is meant to include fluoro, chloro, bromo, and iodo.

According to the method of the present invention, vascular thrombosis in a warm-blooded animal is treated by administering to a warm-blooded animal in need of such treatment an effective amount of a phenoxyphenylacetylene or thio analogue thereof as defined hereinbefore. Such compound can be administered parenterally or enterally, and preferably orally. The compound normally will be administered at a dosage level sufficient to provide a concentration of such a compound in the blood of from about 1 to about 250 µg/ml, and preferably from about 1 to about 100 µg/ml. On the average, such a concentration is approximately equivalent to a dose of from about 0.05 to about 20 mg/kg, with the preferred concentration being approximately equivalent to a dose of from about 0.05 to about 10 mg/kg. The necessary concentration in the blood can be achieved by administering a single dose or up to about six smaller doses per day, depending upon the tolerance of the patient to the compound, persistence of the compound in the blood stream, and other factors. When dosage is oral, the range of administration of such compound normally will be from about 1 to about 150 mg/kg.

Preferably, such compound is employed in combination with one or more adjuvants suited to the particular route of administration. Thus, in the case of oral administration, the compound is modified with pharmaceutical diluents or carriers such as lactose, sucrose, starch powder, cellulose, talc, magnesium stearate, magnesium oxide, calcium sulfate, acacia powder, gelatin, sodium alginate, sodium benzoate and stearic acid. Such a composition can be formulated as tablets or enclosed in capsules for convenient administration. The compound also can be mixed with a liquid and administered as an elixir, suspension, or the like. In the case of parenteral administration, the compound is conveniently formulated in saline to constitute an injectable liquid solution. Other adjuvants and modes of administration are known to those skilled in the art.

Suitable pharmaceutical carriers are described in E. W. martin, et al., "Remington's Pharmaceutical Sciences," 14th Ed., Mack Publishing Company, Easton, Pa., 1965.

The activities of the phenoxyphenylacetylenes and thio analogues thereof as antithrombotic agents are demonstrated by the procedure of Herrmann, et al., *Arch. Int. Pharmacodyn. Ther.*, 196, 316 (1972).

The activities of several of the phenoxyphenylacetylenes and thio analogues thereof relative to parenteral administration were demonstrated by the procedure of Herrmann, et al., *Proc. Soc. Exp. Biol. Med.*, 135, 100 (1970), and references cited therein. Such compounds were found to provide at least about 20 percent inhibition of platelet aggregation.

The activities of such phenoxyphenylacetylenes and thio analogs thereof relative to oral administration were demonstrated by the procedure of Herrmann, et al., *Proc. Soc. Exp. Biol. Med.*, 139, 548 (1972). Such compounds were found to provide at least about 20 percent inhibition of platelet aggregation.

Examples of phenoxyphenylacetylenes and thio analogues thereof suitable for use in the method of the present invention include, among others:

(4-Phenoxyphenyl)acetylene,
(4-Phenylthiophenyl)acetylene,
(3-Phenoxyphenyl)acetylene,
(3-Phenylthiophenyl)acetylene,
(2-Phenoxyphenyl)acetylene,
(2-Methyl-4-phenoxyphenyl)acetylene,
(3-Methyl-3-phenylthiophenyl)acetylene,
(3-Fluoro-4-phenoxyphenyl)acetylene,
(2-Methoxy-4-phenylthiophenyl)acetylene,
[3-(2-Fluorophenoxy)phenyl]acetylene,
[3-(2-Fluorophenylthio)phenyl]acetylene,
[4-(2-Fluorophenoxy)phenyl]acetylene,
[3-(3-Chlorophenoxy)phenyl]acetylene,
[3-(3-Methylphenylthio)phenyl]acetylene,
(3,5-Dimethyl-4-phenoxyphenyl)acetylene,
[4-(2,4-Difluorophenoxy)phenyl]acetylene,
[3-Fluoro-4-(2-fluorophenoxy)phenyl]acetylene, and
[3-(4-Methoxyphenylthio)-4-fluorophenyl]acetylene.

The preferred compounds are the phenoxyphenylacetylenes, with [3-(2-fluorophenoxy)phenyl]acetylene being most preferred.

The phenoxyphenylacetylenes and thio analogues thereof which can be employed in the method of the present invention can be prepared by various known procedures. A preferred procedure is represented by the following reaction scheme, wherein Ar is

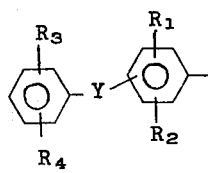

and X is halo:

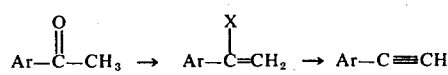

Briefly, an acetophenone is halogenated, typically brominated or chlorinated, to give an α-halostyrene, which on dehydrohalogenation yields the desired arylacetylene compound.

Halogenation of a carbonyl compound generally is carried out with phosphorus pentabromide or phosphorus pentachloride. However, equivalent results are obtained in the above reaction scheme with a mixture of a phosphorus pentahalide and the corresponding phosphorus oxyhalide. While the amounts of the two components employed are not critical, an excess of total available halogen conveniently is employed, the phosphorus oxyhalide also serving as a reaction medium. However, if desired, an inert organic solvent such as benzene, toluene, and the like, can be employed. The halogenation reaction proceeds best at an elevated temperature, e.g., from about 40° to about 200°C. Separation and, if desired, purification of the resulting α-halostyrene are accomplished by conventional means.

Dehydrohalogenation generally is carried out by known methods. Typically, strong bases such as sodium amide, lithium amide, and potassium amide, in liquid ammonia, and potassium t-butoxide in dimethyl sulfoxide give good results. The dehydrohalogenation reaction preferably is carried out at a temperature in the range of from about −30°C. to about 0°C. Separation and purification of the resulting arylacetylene are carried out by known methods.

An alternative method for preparing the arylacetylenes employed in the method of the present invention is illustrated by the following reaction scheme, wherein Ar and X are as defined hereinabove:

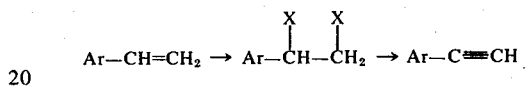

Briefly, a styrene (i.e., an arylethylene) is halogenated to give an α, β-dihaloethylbenzene which subsequently is dehydrohalogenated to give an arylacetylene.

Halogenation of the styrene with chlorine, bromine, or iodine, preferably chlorine or bromine, generally is carried out at a temperature of from about −20° to about 20°C in an inert organic solvent, such as chloroform, methylene chloride, diethyl ether, benzene, toluene, and the like. The usual separation and purification procedures then are employed.

Dehydrohalogenation of the resulting α, β-dihaloethylbenzene to give an arylacetylene in general is carried out as described hereinabove for dehydrohalogenation of the α-halostyrene of the first and preferred procedure.

The acetophenones which are employed as starting materials in the first procedure described hereinabove for preparing arylacetylenes are prepared by methods known to those skilled in the art. Several such methods are illustrated by the following reaction schemes, wherein Ar is as defined hereinbefore:

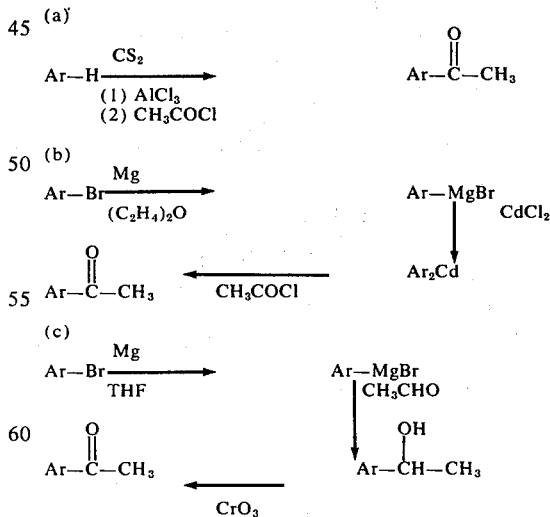

The styrenes employed as starting materials in the alternative procedure described hereinabove for preparing arylacetylenes also are prepared by known methods, such as those illustrated by the following reaction schemes, wherein Ar is as defined hereinbefore:

(d)

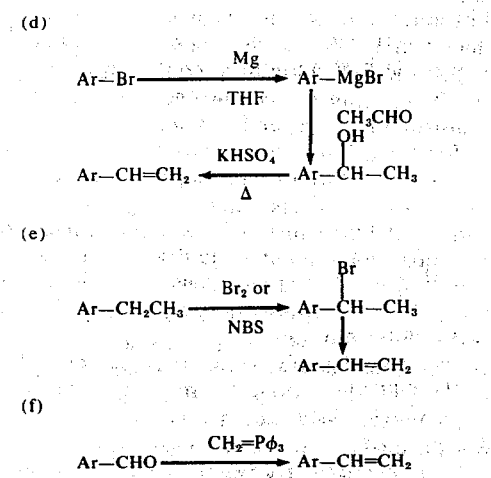

(e)

(f)

Preparations representative of several of the methods for preparing acetophenones follow.

Reaction Scheme (a).

A solution of 200 g of 2-fluorobiphenyl in 1500 ml of carbon disulfide was cooled to 0°–5°C and successively treated with 200 g of aluminum chloride over a period of 140 minutes and 113 g of acetyl chloride over a period of 165 minutes. The resulting mixture was allowed to warm to room temperature and stirred overnight. The reaction mixture then was poured carefully into a mixture of ice and aqueous hydrochloric acid. Organic materials were extracted from the resulting acidic mixture with a mixture of diethyl ether and ethyl acetate. The organic extract was washed successively with water, ten percent aqueous sodium hydroxide, and water, and dried over anhydrous sodium sulfate. The solvents were evaporated under reduced pressure and the solid residue was recrystallized from hexane to give 4'-(2-fluorophenyl)acetophenone. Recrystallization of the material from hexane gave two crops of crystals having the following elemental analyses:

First crop, 173 g, mp 84.5°–86.5°C; calculated for $C_{14}H_{11}FO$: C, 78.49; H, 5.18; F, 8.87. Found: C, 77.23; H, 4.75; F, 10.00. Second crop, 51.1 g, mp 85°–87°C Found: C, 78.40; H, 5.35; F, 8.89.

Reaction Scheme (b).

3-Biphenylmagnesium bromide was prepared according to known procedures from 100 g of 3-bromobiphenyl and 10 g of magnesium turnings in diethyl ether. To the Grignard reagent solution at 4°C was added 40 g of cadmium chloride dihydrate over a one-hour period. The reaction mixture was heated at reflux for one hour and cooled to 12°C. To the reaction mixture then was added a solution of 32 g of acetyl chloride in diethyl ether over a period of 30 minutes. The reaction mixture was heated at reflux for 30 minutes, allowed to cool to room temperature, and agitated overnight. Additional diethyl ether was added and the reaction mixture again was heated at reflux for one hour. The reaction mixture was cooled and successively treated with 100 ml of saturated aqueous ammonium chloride and 100 ml of water. The reaction mixture was poured over ice, the diethyl ether layer which formed was separted, and the aqueous layer was extracted with diethyl ether. The diethyl ether layer and extracts were combined, washed successively with water until the wash water was neutral to litmus paper, and dried over anhydrous sodium sulfate. The diethyl ether was evaporated and the residue was vacuum distilled to give 29.3 g of 3'-phenylacetophenone, bp 120°C/0.3 mm. The following elemental analysis was obtained:

Calculated for $C_{14}H_{12}O$: C, 85.68; H, 6.16; O, 8.15. Found: C, 85.62; H, 6.33; O, 8.18.

Reaction Scheme (c).

2-Chloro-4-biphenylmagnesium bromide was prepared by known methods from 53.4 g of 2-chloro-4-bromobiphenyl and 5.0 g of magnesium turnings in tetrahydrofuran. A solution of 9.2 g of acetaldehyde in 100 ml of tetrahydrofuran was added dropwise to the cooled Grignard reagent solution. The reaction mixture was stirred at room temperature overnight. The reaction mixture then was cooled, treated successively with 165 ml of saturated aqueous ammonium chloride and 100 ml of water, and poured onto ice. The reaction mixture was extracted with diethyl ether. The diethyl ether extracts were combined, washed three times with water, and dried over anhydrous sodium sulfate. The diethyl ether was evaporated under reduced pressure and the liquid residue was vacuum distilled to give 28.6 g of α-methyl-3-chloro-4-phenylbenzyl alcohol, bp 145°–157°C/0.09 mm. The following elemental analysis was obtained:

Calculated for $C_{14}H_{13}ClO$: C, 72.26; H, 5.63; O, 6.88. Found: C, 71.98; H, 5.79; O, 6.90.

α-Methyl-3-chloro-4-phenylbenzyl alcohol, 28.6 g, was dissolved in 36 ml of acetone. To the resulting solution was added dropwise, with cooling and vigorous agitation, a solution of 12 g of chromium trioxide in 42 ml of 35 percent aqueous sulfuric acid. A large volume of acetone then was added; the aqueous layer was separated and washed with acetone. The acetone layer and acetone extracts were combined and dried over anhydrous sodium sulfate. The acetone was evaporated and the residue was distilled in vacuo to give 26.3 g of 3'-chloro-4'-phenylacetophenone, bp 132°–141°C/0.09 mm. The following elemental analysis was obtained:

Calculated for $C_{14}H_{11}ClO$: C, 72.89; H, 4.81. Found: C, 72.63; H, 4.85.

The present invention is further described, but not limited, by the following examples which illustrate preferred procedures for the preparation of the arylacetylenes to be employed in the present invention. All temperatures are in degrees centigrade.

EXAMPLE 1

Preparation of [3-(2-fluorophenoxy)phenyl]acetylene.

A mixture of 34.5 g of 4'-(2-fluorophenoxy)acetophenone, 41.6 g of phosphorus pentachloride, and 80 ml of phosphorus oxychloride was heated at 60° for 20 hours. The reaction mixture was cooled and volatile materials were distilled in vacuo. The crude 4-(2-fluorophenoxy)-α-chlorostyrene which remained was diluted with benzene which was removed by distillation; the dilution-distillation procedure was repeated three times. The residue then was dissolved in tetrahydrofuran. The resulting solution was added dropwise to a solution of sodium amide in ammonia prepared by adding 23 g of sodium to 750 ml of liquid ammonia containing several mg of ferric chloride. The reaction solution was agitated overnight after adding 375 ml of diethyl ether. The reaction solution then was diluted successively with 150 ml of saturated aqueous ammonium chloride solution and 100 ml of water. The resulting mixture was poured onto ice. The organic layer was separated and the aqueous layer extracted successively with diethyl ether and ethyl acetate. The organic layer and organic extracts were combined and washed successively with water, five percent aqueous hydrochloric acid, and water, and dried over anhydrous sodium sulfate. The organic solvents were distilled under reduced pressure and the residue was vacuum distilled to give [3-(2-fluorophenoxy)phenyl]acetylene, bp 93°–96°/0.2 mm. The following elemental analysis was obtained:

Calculated for $C_{14}H_9FO$: C, 79.23; H, 4.27; F, 8.95. Found: C, 78.95; H, 4.30; F, 8.71.

EXAMPLE 2

The following compounds were prepared from the indicated ketone according to the procedure of Example 1, using appropriate amounts of phosphorus pentachloride, phosphorus oxychloride, sodium amide, and ammonia; the elemental analysis of each compound also is given:

(2-Methyl-4-phenoxyphenyl)acetylene, bp 110°–122°/0.35 mm and $n_d^{25}$, 1.5994; from 2'-methyl-4'-phenoxyacetophenone.

Calculated for $C_{15}H_{12}O$: C, 86.51; H, 5.81; O, 7.68. Found: C, 86.24; H, 6.02; O, 7.63.

(3-Methyl-4-phenoxyphenyl)acetylene, bp 103°–105°/0.1 mm and $n_d^{23}$, 1.5949; from 3'-methyl-4'-phenoxyacetophenone.

Calculated for $C_{15}H_{12}O$: C, 86.51; H, 5.81; O, 7.68. Found: C, 86.42; H, 5.81; O, 7.39.

(3-Phenoxyphenyl)acetylene, bp 90°/0.2 mm and $n_d^{23}$, 1.5987; from 3'-phenoxyacetophenone.

Calculated for $C_{14}H_{10}O$: C, 86.57; H, 5.19; O, 8.24. Found: C, 86.30; H, 5.18; O, 8.04.

(3,5-Dimethyl-4-phenoxyphenyl)acetylene, bp 145°–146°/0.1 mm and $n_d^{25}$, 1.5882; from 3',5'-dimethyl-4'-phenoxyacetophenone.

Calculated for $C_{16}H_{14}O$: C, 86.45; H, 6.35; O, 7.20. Found: C, 86.20; H, 6.37; O, 7.17.

[4-(2-Fluorophenoxy)phenyl]acetylene, bp 110°–114°10.3 mm and $n_d^{25}$, 1.5860; from 4'-(2-fluorophenoxy)acetophenone.

Calculated for $C_{14}H_9FO$: C, 79.23; H, 4.27. Found: C, 79.00; H, 4.41.

As pointed out hereinbefore, the treatment of vascular thrombosis by the method of the present invention, and by antithrombotic agents in general, largely is prophylactic in nature. Such prophylaxis comprises the administration of an antithrombotic agent to an individual based upon a need of the individual for such administration. In general, an individual will have a need for treatment with antithrombotic agents under either of two situations: (1) the individual already has suffered overt manifestations of a thromboembolic disease, or (2) an individual has an identifiable risk of contracting a thromboembolic disease but has not yet shown any overt manifestations of such disease. In either case, the prophylactic treatment of the individual with an antithrombotic agent is intended to prevent thromboembolic disease in the individual or, at least, to minimize the effects of such disease upon the health of the individual should such disease occur.

What is claimed is:

1. A method of treating vascular thrombosis in warm-blooded animals which comprises administering to a warm-blooded animal in need of such treatment an amount effective for treating vascular thrombosis of a phenoxyphenylacetylene of the formula,

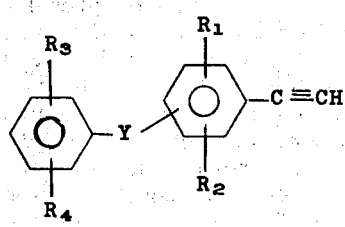

wherein $R_1$, $R_2$, $R_3$, and $R_4$ are monovalent groups independently selected from the group consisting of hydrogen, halo, $C_1$–$C_3$ alkyl, and $C_1$–$C_3$ alkoxy; and Y is oxygen.

2. The method of claim 1, wherein $R_1$, $R_2$, $R_3$, and $R_4$ independently are hydrogen, fluoro, chloro, methyl, or methoxy.

3. The method of claim 1, wherein $R_1$, $R_2$, $R_3$, and $R_4$ independently are hydrogen or fluoro.

4. The method of claim 3, wherein the phenoxyphenylacetylene is [3-(2-fluorophenoxy)phenyl]acetylene.

* * * * *